United States Patent [19]

Andrew

[11] 4,328,780
[45] May 11, 1982

[54] GAS ANALYSIS

[75] Inventor: Sydney P. S. Andrew, Stockton-on-Tees, England

[73] Assignee: Imperial Chemical Industries Limited, London, England

[21] Appl. No.: 9,073

[22] Filed: Feb. 2, 1979

[30] Foreign Application Priority Data

Feb. 3, 1978 [GB] United Kingdom ................. 4442/78

[51] Int. Cl.³ ............................................. F02M 7/00
[52] U.S. Cl. .................................. 123/440; 23/232 E; 60/276; 73/27 R; 422/93
[58] Field of Search ....... 123/32 EE, 119 EC, 119 A, 123/119 E; 60/276, 303; 73/27 R; 422/93, 78; 23/230 PC, 232 E

[56] References Cited

U.S. PATENT DOCUMENTS

| | | | |
|---|---|---|---|
| 1,333,850 | 3/1920 | Kennedy | 23/232 E |
| 1,993,665 | 3/1935 | Holt | 123/119 E |
| 3,825,239 | 7/1974 | Rice | 73/26 |
| 3,841,283 | 10/1974 | Wood | 123/119 EC |
| 3,846,076 | 11/1974 | Henault | 123/32 EE |
| 3,863,615 | 2/1975 | Pagdin | 123/119 A |
| 3,885,540 | 5/1975 | Stadler | 123/119 A |
| 4,130,397 | 12/1978 | Robitaille | 60/303 |
| 4,144,855 | 3/1979 | Masui et al. | 123/119 EC |
| 4,169,708 | 10/1979 | Muggli | 422/93 |

FOREIGN PATENT DOCUMENTS

| | | | |
|---|---|---|---|
| 970434 | 9/1964 | United Kingdom | 23/230 PC |
| 1285954 | 8/1972 | United Kingdom | . |
| 1391514 | 4/1975 | United Kingdom | . |
| 1444362 | 7/1976 | United Kingdom | . |

*Primary Examiner*—Charles J. Myhre
*Assistant Examiner*—Andrew M. Dolinar
*Attorney, Agent, or Firm*—Cushman, Darby & Cushman

[57] ABSTRACT

In a gas analysis method and apparatus especially suitable for controlling the inlet air to fuel ratio of a lean-running internal combustion engine, combustion effluent gas is divided into a plurality of part streams, there is added to a first part stream whichever of a combustible and a combustion-supporting constituent it is deficient in, combustion is effected and the temperature difference between the streams is measured. Preferably the temperature difference is measured by reference to the magnitude of the electric current required to heat an untreated part stream to the temperature of a part stream heated by combustion due to the added constituent. Preferably the temperature sensor used acts as a catalyst for the combustion and as a heating element, so that combustion takes place only in the vicinity thereof. Gas flow through the apparatus is preferably effected by a constant vacuum engine intake.

23 Claims, 5 Drawing Figures

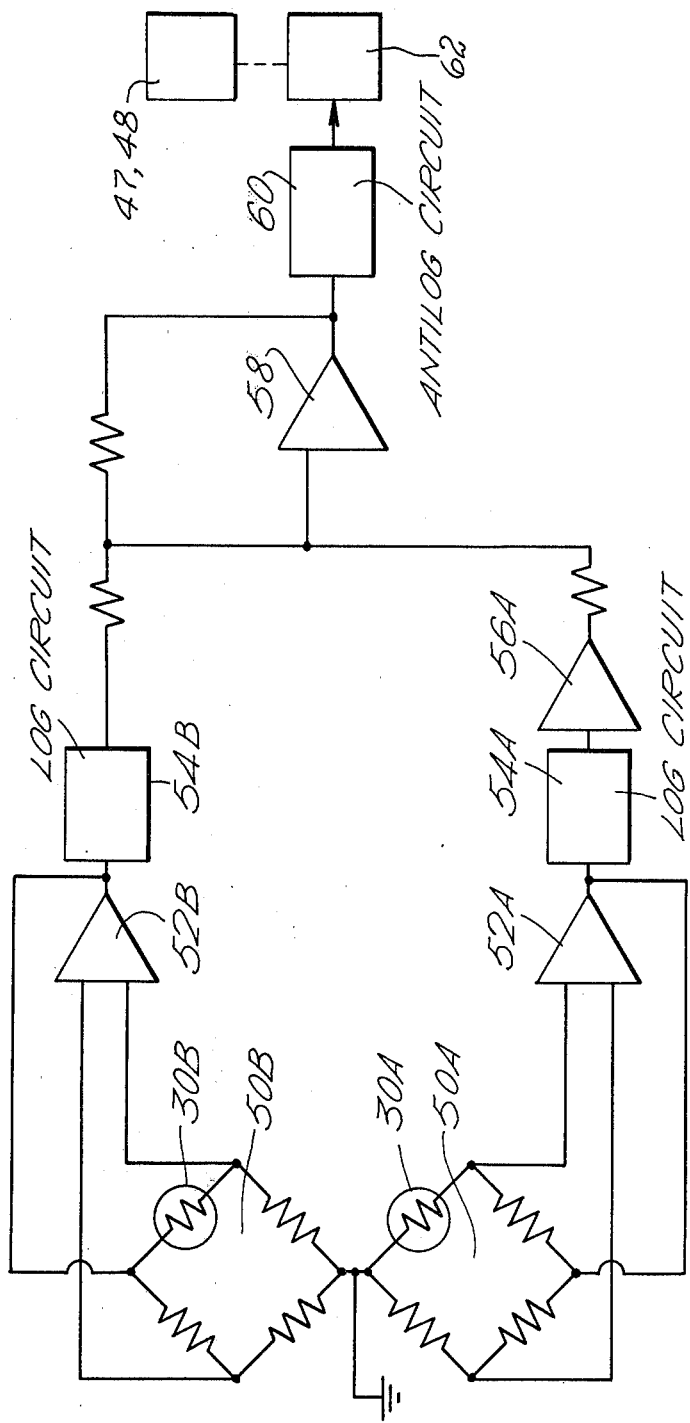

GAS ANALYSIS

This invention relates to gas analysis and in particular to a method and apparatus for analysing combustion effluent gas for combustible or combustion-supporting constituents, and to an internal combustion engine in combination with such apparatus.

In order to control the efficiency of combustion operations and the content of undesirable constituents, such as nitrogen oxides in combustion effluent gas, it has become necessary to measure the oxygen content of combustion effluent gases accurately and reliably and to derive from such measurement an electrical signal. Proposals have been made to measure the oxygen content by means of an oxygen-sensitive electrode. These can be embodied in systems that are mechanically simple but they inherently suffer from the defect that the electric potential of the electrode is proportional to logarithm of the ratio of the oxygen content of the effluent to that of air. As a result they are as sensitive to a tenfold change of oxygen partial pressure from say 0.1% to 0.01% as to a change from 10% to 1%, but are much less sensitive to a twofold change of oxygen partial pressure from say 0.5% to 1.0% such as would be critical in controlling operation of some types of internal combustion engine consuming a "lean" air-fuel mixture. They have the further defect that the magnitude of the electrode potential is very low unless the said ratio is very large, so that complicated electrical circuitry is required unless the desired oxygen concentration is extremely low.

A method and apparatus according to the present invention have been devised for gas analysis that have a sensitivity characteristic suitable for combustion gas mixtures of moderate oxygen content, for example those liable to fluctuate in the range of 0.01 to 5% by volume. They are also suitable, with modification, for gases in which combustibles are present and oxygen is in deficiency if present at all.

According to the invention a stream of combustion effluent gas is analysed for combustible or combustion-supporting constituents by the steps of (a) forming a plurality of part streams of such gas;

(b) adding to a first part stream whichever of a combustible and a combustion-supporting constituent it is deficient in;

(c) subjecting a second, untreated, part stream and gas from step (b) to conditions effective to cause mutual reaction of combustible and combustion-supporting constituents; and (d) measuring the temperature difference between the two part streams after subjection to those conditions.

In an important application of the method effluent is the exhaust of an internal combustion engine, especially a reciprocating spark-ignition engine. Whereas for convenience in operation such engines have been designed to consume a "rich" gasoline-air mixture in which gasoline is slightly in excess, a decrease in the quantity of unburnt and partially burnt gasoline and hence a decrease in air pollution from such engines and an increase in thermal efficiency is secured by running 'lean', with a slight excess of air. Such close control of the mixture ratio in the lean range can be effected by using the analysis to correct, through a feed-back device, the setting of the carburetor or gasoline-injection system. A particular example of such a slightly lean engine is one operating at an air to fuel weight ratio in the range 14.8 to 17.0 especially up to 15.8. The linear response of the technique according to the invention makes it very suitable for detecting and correcting departures from a desired level within such a range. Engines having a compression ratio over 8.0 especially in the range 10-14 as now being developed, are very suitable for application of the method. In order to detect over-lean running a combustible is added at step (b). If it is necessary to detect over-rich running, air is added at step (b). If it is desired to control the inlet mixture within limits of richness and leanness, two forms of the analysis method can be operated simultaneously or alternatingly, one with combustible addition, the other with combustion-supporting addition.

In especially useful embodiments of the invention the mutual reaction in step (c) does not involve the whole of the part stream but takes place mainly or exclusively in the immediate vicinity of the sensor used to measure the temperature. As a result, thermal effects are minimised and the construction of the necessary apparatus can be simplified. The desired localised reaction can be achieved by means of a catalytic element, comprising for example platinum or a platinum alloy or other platinum group metals and alloys, close to the temperature sensor. Such an element may be provided with means, such as an electric resistance, for heating it, at least at the time of starting the analysis from cold. The temperature resulting from the mutual reaction is typically in the range 600°–800° C.

Temperature measurement is preferably by electrical means, especially by resistance wires or by a thermocouple. Using a thermocouple the catalytic element and its heater, if any, is normally separate from the sensor. A resistance wire can, however, act also as the catalyst and the heater and is therefore preferred as the temperature sensor.

Measurement of temperature difference can be carried out in a direct way but is preferably done by electrically heating the combustion-free part stream to a measured extent. That is, such measurement comprises feeding an electric current to a heating element in the untreated part stream, feeding no or a smaller current to the part stream heated by combustion, and adjusting the current until the temperatures measured are equal or differ by a specified amount. This method is especially suitable using a resistance wire as temperature sensor, heater and catalyst since then the quantities of gas to be heated and the electrical load involved are minimal.

The method may include an equilibration step before step (b) and preferably before step (a) in which any residual oxygen and unburnt combustibles in the gas are reacted together. The resulting higher temperature is advantageous when addition of the combustible in step (c) is by evaporation of a liquid, for example gasoline. In contrast with preferred forms of step (c), all the gas should react in the equilibration step.

Passage of the combustion effluent gas through zones corresponding to steps (a) to (c) is conveniently effected by suction. In an internal combustion engine the gas passes from step (c) preferably to the engine inlet: such as the inlet of a supercharging pump or, more commonly to a carburetor or fuel-injection system. The streams of gas subjected to steps (a) to (c) normally are small enough not to affect significantly the composition of the engine inlet mixture. If desired, the method can be applied to an engine operated with exhaust gas recycle, in which event the streams can be fed to the recycle pump inlet. It is also within the invention to use a suction means feeding the engine inlet but separate from means provided for normal operation of the engine.

Preferably the suction means operates at a substantially constant pressure-drop, so as to avoid significant fluctuations in the rate of flow through the zones. In an unsupercharged engine this is conveniently effected by an air intake having a variable choke the aperture area of which is automatically adjusted by a piston subjected to the pressure obtaining on the engine side of the choke. The outlet of step (c) is connected to the intake downstream of the variable choke. Such an air intake can be as used in the SU (trademark) carburetor, or carburetors of similar type, in their vertical or horizontal arrangement. Other types of constant pressure-drop air intakes, including those used in carburetors, can be used.

In order to make the suction rate steadier, the gas inlet to step (a) is connected to the air intake upstream of the variable choke. This connection is downstream of any air filter or other air-treatments. By this means the pressure drop across the analysis section is balanced with that across the induction air valve. Further, a more even suction can be obtained by means of a reservoir. The reservoir need, however, not be separate but can be one used for other duties such as powering brakes. Fluctuation in exhaust gas pressure at the inlet of step (a) can be smoothed out by a flow constriction.

The method is especially convenient for use with an engine having a constant pressure-drop carburetor such as of the "SU" type in which a fuel needle valve and a variable choke are automatically adjusted by a piston as mentioned. In such an engine no separate suction intake for the gas leaving step (c) is needed.

A description of the "SU" carburetor is given in "The Motor Vehicle" by Newton and Steeds, published by Iliffe, London 1953.

The invention provides, as apparatus (referred to in the drawing as the "detector") for carrying out the analysis, the combination of:

(a) an inlet for combustion effluent gas including a flow-dividing zone providing a plurality of part streams of such gas;

(b) a plurality of addition zones including means to add a combustible constituent or combustion-supporting constituent to one of two such part streams or each of such constituents to one of three such part streams, in either case leaving one untreated part stream; and (c) a plurality of reaction zones each receiving separately a stream from zone (b) and including a temperature sensor.

The detector may include, preferably upstream of the flow-dividing zone, at least one equilibration zone having an inlet for combustion effluent gas, a pre-reaction region (suitably electrically heated and/or containing an oxidation catalyst such as a platinum group metal, possibly in the form of an electrically heated wire) and an outlet for equilibrated gas. The flow-dividing means may be constituted by two or more passages acting as the outlet of the equilibration zone.

There is preferably a flame trap between the equilibration zone (if present) and the addition zone, and between the addition zone and the reaction zone.

The temperature sensor preferably includes one or more electrical resistance wires. The resistance can be measured by a conventional bridge circuit. Instead of balancing such a bridge circuit rheostatically, the resistance can be effectively measured by electrically heating the untreated stream and measuring the power input required in order to equalise or bring to a specified level of difference the temperatures of the streams and thus the resistances of the wires. Preferably both the untreated and the combustion stream are electrically heated to some temperature above that likely to be reached by combustion alone. The apparatus therefore preferably includes means to heat electrically the untreated stream and preferably also the combustion stream. Such heating means is preferably the same element as is used to measure resistance, so that only the temperature of the gas in contact with the element is measured.

Alternatively the temperature sensor can be a thermocouple junction. The "hot" junction can be in the combustion stream and the reference junction in the untreated stream, in which event the electromotive force (e.m.f.) generated is proportional to the temperature difference and thus to the oxygen or fuel content of the exhaust gas. If the electric heating method is used, the electric input power required to produce a zero e.m.f. is measured. Systems having a reference junction at another temperature, such as ambient air, can be used. In thermocouple systems, the electric heating element is normally distinct from the temperature sensor, but preferably the two are disposed close together.

The invention includes the combination of the detector and the electrical circuit effective to generate an electrical signal from the output of the temperature-sensors. Such a circuit may include an amplifier and preferably includes a differential amplifier the input terminals of which are connected to opposite angles of a resistance-measuring bridge. In the system using electric heating of a gas stream, there is preferably a connection from the output of such a differential amplifier to one angle of the bridge, so that the amplifier supplies the power required to heat the gas. When more than one stream is heated, such a bridge and amplifier are coupled to each heater/resistance element combination. The power outputs of the amplifiers can be measured by reference to the voltage each applies to its respective bridge. The outputs can be compared suitably by feeding each to a circuit having an output varying as the logarithm of its input, subtracting one logarithmic output from the other and feeding the difference to a circuit having an output varying as the anti-logarithm of its input. The output of such a circuit is proportional to the extent of combustion in the exhaust gas.

The combination of the detector and electrical circuits can be combined further with means to give a warning to a human operator or, more usefully, to adjust the inlet air-to-fuel ratio of the combustion operation. The adjustment involves a simple electromechanical actuator and need not be detailed. When the air/fuel mixture is produced in an "SU" type carburetor, adjustment can be applied to the screw mounting of the nozzle of the needle valve or to the partial vacuum chamber controlling the position of the piston and thus the setting of the choke and the needle of the valve. The electrical circuits can be programmed to take account of the differing air-to-fuel ratios according to driving conditions; a computer controlling both the engine air-to-fuel ratio and transmission gear ratio is envisaged.

Thus the invention comprises an internal combustion engine with means for control by the method or apparatus described herein. Particularly it includes the flow connections from the exhaust to the inlet of the detector, and from the detector to the engine inlet, in preference to an ejector or suction pump. The engine is especially one designed to operate at the air-to-fuel ratio and compression ratio specified above. The feed of fuel to zone (c) (if such a feed is used) can be effected by a connection to the engine fuel system, for example, by means of a wick leading to the carburetor float chamber, which can provide sufficient fuel to saturate the gas at the operating temperature and pressure. If an air feed is required to one of zones (c), this can be effected by carburetor suction. The zones and their intervening flame traps can be provided in a single vessel, which thus can be compactly disposed in the engine compartment of an automobile.

Preferred forms of the invention are shown in the accompanying drawings in which FIG. 1 shows one type of detector and its connections to the exhaust pipe and carburetor of an internal combustion engine;

FIG. 3 shows an electrical circuit suitable for converting the electrical signals from the detector.

Figure 1:
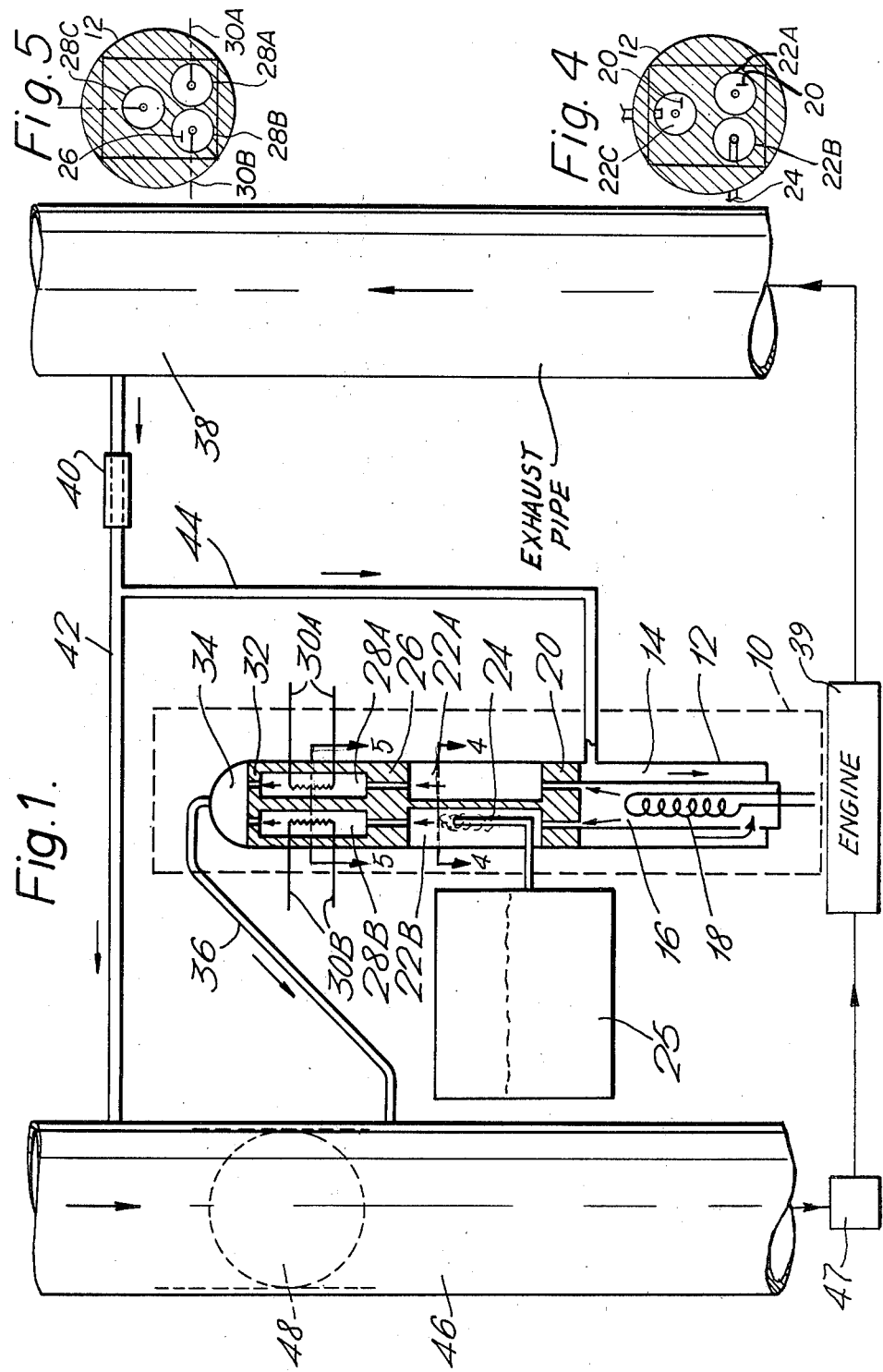

FIGS. 4 and 5 are schematic cross-sectional views taken along lines 4—4 and 5—5 of FIG. 1, respectively.

Referring to FIG. 1, the detector 10, bounded by the pecked lines, comprises a cylindrical vessel 12 formed essentially with the following chambers 14 a preheat chamber;
16 the reaction chamber forming the equilibration zone and heated by electric heater 18. Flame trap 20, a metal block having two (or possibly three) narrow passages in it, closes the end of chamber 16 and constitutes the flow-dividing means;
22A and 22B forming the addition zones, each fed by one of the passages in flame trap 20. As shown, chamber 22A has no means for adding anything and thus carries the blank gas stream. Chamber 22B is equipped with wick saturator 24 feeding gasoline into the gas stream. If desired, a third chamber 22C (FIG. 4) with air addition means could be used, or such a chamber could be used in place of 22B if departure from lean to rich engine feed is to be detected. Flame trap 26, a metal block having two (or possibly three) narrow passages in it, closes the downstream end of chambers 22;
28A and 28B forming the reaction zones. These may be formed in the same metal block providing flame trap 26. If desired, one of chambers 28 can correspond with chamber 22C, whether used as a third chamber or as an air-addition chamber instead of a fuel-addition chamber. Each chamber 28 is heated by a hot platinum wire 30, each of which both provides the heat necessary to cause reaction to take place and acts as a catalyst and as a sensor of the temperature of the gas in immediate contact with it. Chambers 28 are closed at their downstream end by flame trap 32.
34 a collecting chamber, with an outlet into pipe 36. (Pipe 36 may include a reservoir additional to the capacity provided by chamber 34).

Exhaust gases from pipe 38 pass through restrictor 40 and are divided into a by-pass stream in line 42 and an analysis stream entering detector 10 via line 44. Pipe 38 is preferably the exhaust pipe from an internal combustion engine, illustrated schematically at 39 in FIG. 1. The gases are preheated in chamber 14 and then pass into chamber 16 where any $H_2$, CO and residual hydrocarbon react with any residual oxygen. Fuel is supplied from carburetor float chamber 25, added to the part stream entering chamber 22B and the two part streams pass into respective chambers 28A and 28B. If the exhaust gas contains excess oxygen, combustion takes place in chamber 28B and raises the temperature to a higher level than that of chamber 28A, thus increasing the resistance of wire 30B to a higher level than that of 30A. (An analogous temperature increase would occur in chamber 28C (FIG. 5) if the exhaust gas contained excess combustible material and air were added in chamber 22C). The difference in temperature is measured in a bridge or like circuit such as that shown in FIG. 3. The reacted gases leave detector 10 under the suction of the partial vacuum in inlet pipe 46 of the SU carburetor 47, or the like. Pipe 42 balances the pressure-drop through the detector with that across induction air valve 48. The structures 46, 48 normally are part of the SU carburetor (see "The Motor Vehicle" by Newton and Steeds, discussed earlier).

The resistance-measuring circuit may feed a servo-mechanism 62 (see FIG. 3) actuating valve 48 and/or a gasoline inlet valve.

Figure 2:
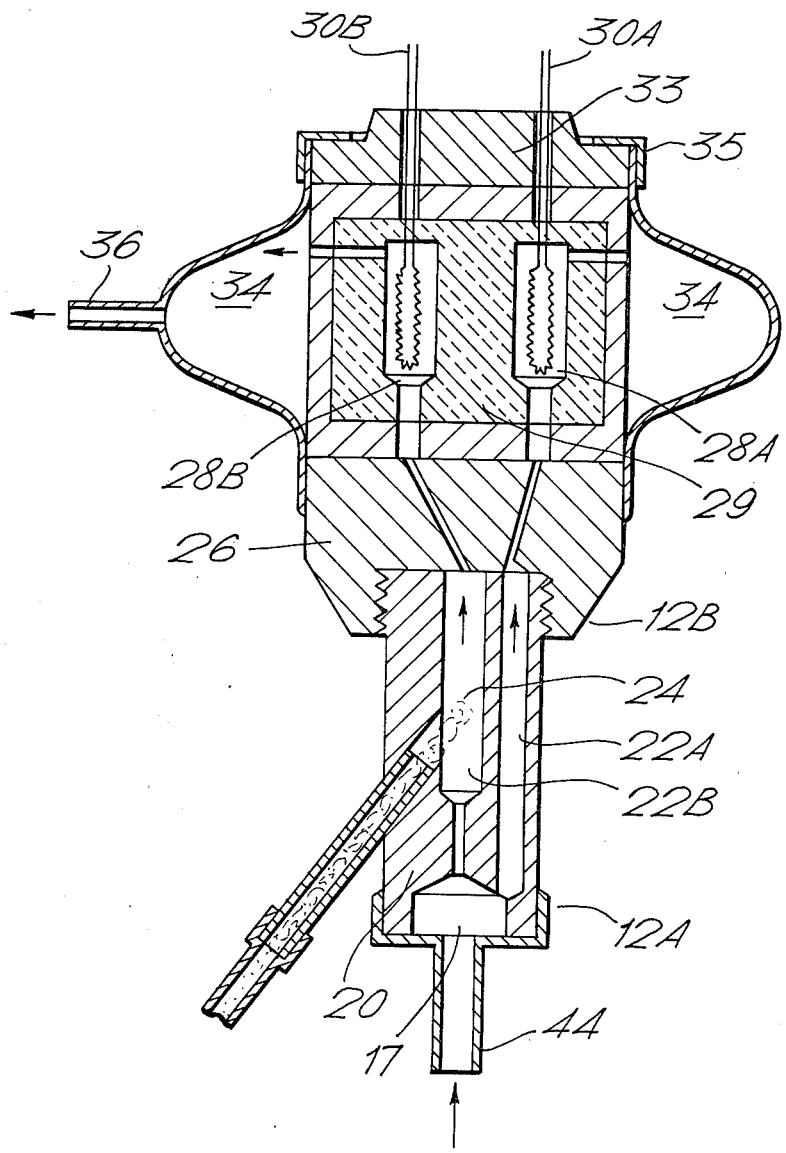
FIG. 2 shows an alternative type of detector.

The detector shown in FIG. 2 differs from that of FIG. 1 in not including equilibration zone 18. It is contained within a generally cylindrical vessel having a fuel-addition section 12A screwed into a reaction section 12B. Section 12A includes plenum chamber 17 feeding zone 22A directly and 22B via a narrow passage constituting a flame trap in metal block 20. As in FIG. 1 zone 22A carries the blank gas stream but 22B is equipped with wick saturator 24 feeding gasoline into the gas stream. Flame trap 26 is a metal block having two narrow passages in it and, when screwed on to section 12A, closes the downstream end of zones 22A and 22B and provides their outlets into reaction zones 28A and 28B respectively. Section 12B includes three main zones, namely flame trap 26 already referred to, reaction zones 28A and 28B within refractory insulated block 29 and collecting chamber 34, which is of greater volume than in the detector of FIG. 1, in order to smooth out variations in the suction applied by the engine inlet. Each zone 28 is heated by a hot catalytic wire 30 and discharges into chamber 34. Section 12B is closed at its upper end by an electrically insulating cover 33 held in place by screw-on end cap 35, so as to provide ready access for inspection and for replacing heating wires 30 if required.

The mode of action is generally the same as in FIG. 1 except that, in the absence of the equilibration zone, there may be a small instead of a zero heat generation in the blank gas stream 22A-28A.

The modification of this detector to detect and measure excess combustible material in an exhaust gas is analogous to what was described in relation to FIG. 1.

Referring to FIG. 3, the heated resistance thermometer wires 30A and 30B each constitute one member of a resistance bridge 50A or 50B, each of which feeds high output current differential amplifier 52A or 52B respectively, the output of which is fed to wires 30A and 30B acting as heaters and measured and converted to logarithmic form in circuits 54A or 54B, respectively. The logarithmic output of circuit 54A is inverted in amplifier 56A and the difference between the resulting output and that of circuit 54B is fed to summing amplifier 58 and antilog circuit 60. The output of circuit 60 is proportional to the oxygen content of the exhaust gas and can be fed to a controller 62 effective to vary the air/fuel ratio of a carburetor 47. In the detector as shown wire 30A is in the blank stream and thus receives a relatively large power input from amplifier 52A, sufficient to raise the gas temperature to a predetermined level higher than is expected to occur in the combustion stream. Wire 30B is normally heated by combustion and thus receives only a small electric power input in order to raise its temperature to the predetermined level.

I claim:

1. A method of analyzing for combustible or combustion supporting constituents an exhaust gas of an internal combustion engine having an air intake, including an induction air valve comprising the steps of:
   (a) applying suction with the air intake to the exhaust gas to withdraw a sample stream thereof;
   (b) forming a plurality of part streams of the sample stream, including first and second part streams;
   (c) adding to the first part stream whichever of a combustible or combustion supporting constituent it is deficient in;
   (d) subjecting the gas in the first stream, after step (c), and the second, untreated, part stream, to conditions effective to cause mutual reaction of combustible and combustion-supporting constituents;
   (e) measuring the temperature difference between the first and second part streams after each is subjected to the conditions of step (d);
   (f) allowing the first and second part streams, after step (e), to pass into the air intake under the influence of the applied suction from the air intake;
   after step (a) and independently of step (b): (g) dividing the sample stream into a bypass stream and an analysis stream, said analysis stream being further acted upon in step (b);
   (h) passing the bypass stream directly to the air intake upstream of the induction air valve; and
   practicing step (f) so that the first and second part streams enter the air intake downstream of the induction air valve, the bypass stream balancing the pressure drop through steps (a)–(e) with that across the induction air valve.

2. A method as recited in claim 1 comprising the further step of, before adding to the first part stream whichever of a combustible or a combustion-supporting constituent it is deficient in, practicing an equilibration step wherein any residual oxygen and unburnt combustibles in the gas are reacted together.

3. A method as recited in claim 2 wherein said further step is practiced by passing the gas past an electric heater heated to a temperature higher than the temperature of the exhaust gas immediately after exhausting from the engine.

4. A method as recited in claim 2 comprising the still further step of preheating the gas before practicing said further step.

5. A method according to claim 1 in which the temperature difference is measured by feeding an electrical current to a heating element in the untreated part stream, feeding no or a smaller current to a heating element in the part stream heated by combustion, adjusting the current until the temperatures measured are equal or differ by a specified amount and comparing the magnitudes of the currents fed.

6. A method according to claim 5 in which a resistance wire acts as a heater, catalyst and temperature sensor.

7. A method according to claim 1 in which the gas is the exhaust of an internal combustion engine operated at an air to fuel weight ratio in the range 14.8 to 17.0.

8. A method according to claim 1 in which the mutual reaction is effected by a catalytic element disposed close to a temperature sensor employed in practicing step (e).

9. A method as recited in claim 8 wherein the mutual reaction is further effected by providing the catalytic element integral with the temperature sensor.

10. A method as recited in claim 1 wherein step (a) is practiced so that the withdrawn sample is small enough not to significantly affect the composition of the engine inlet mixture.

11. Apparatus for analyzing exhaust gas from an exhaust pipe of an internal combustion engine having a suction air intake for combustible or combustion-supporting constituents, said suction air intake including an induction air valve, said apparatus comprising:
   a detector including means for separating a gas stream into a plurality of part streams, including first and second part streams, means for adding to the first part stream whichever of a combustible or combustion-supporting constituent it is deficient in, means for subjecting the first stream after such addition, and for subjecting the second untreated stream, to conditions effective to cause mutual reaction of combustible or combustion-supporting constituents, and means for measuring the temperature difference between the first and second part streams after being acted upon by said subjecting means;
   means for connection between said detector and the exhaust pipe for withdrawing a sample stream of gas from the exhaust pipe and passing it to said detector;
   means for connection between said detector and the suction air intake downstream of said induction air valve, for passing the first and second part streams after passage through said measuring means to the suction air intake; and
   means for balancing the pressure drop through said detector with that across the induction air valve.

12. Apparatus as recited in claim 11, wherein said balancing means comprises means for dividing said withdrawn sample into a bypass stream, and an analysis stream operatively connected to said detector, and means for introducing said bypass stream upstream of the induction air valve in the air intake.

13. Apparatus as recited in claim 11, wherein said detector further comprises means for heating the exhaust gas, before passage thereof to said subjecting means, to a temperature sufficient to react any residual oxygen and unburnt combustibles in the exhaust gas stream.

14. Apparatus as recited in claim 11, wherein said detector further comprises:
   an electric heating element associated with said subjecting means and said measuring means, and means for feeding an electric current to said heating element, means for adjusting the current until the temperature measured in the untreated stream is equal to or differs by a specified amount from the temperature measured in a stream in which combustion is taking place, and means for measuring the magnitude of the current.

15. Apparatus for analyzing exhaust gas from an exhaust pipe of an internal combustion engine having a suction air intake for combustible or combustion-supporting constituents, comprising:
   a detector including means for separating a gas stream into a plurality of part streams, including first and second part streams, means for adding to the first part stream whichever of a combustible or combustion-supporting constituent it is deficient in, means for subjecting the first stream after such addition, and for subjecting the second untreated stream, to conditions effective to cause mutual reaction of combustible and combustion-supporting constituents, means for measuring the temperature difference between the first and second part streams after being acted upon by said subjecting means, and means for heating the exhaust gas, before passage thereof to said subject means, to a temperature sufficient to react any residual oxygen and unburnt combustibles in the exhaust gas stream, said heating means comprising an electric heating element disposed in a chamber surrounded by a preheat chamber for the exhaust gas; gas passing from the exhaust pipe passing first through said preheat chamber and then into said electric heating element chamber, and wherein said detector separating means comprise means defining a plurality of exit openings in a flame trap bordering said electric heating element chamber;

means for connection between said detector and the exhaust pipe for withdrawing a sample stream of gas from the exhaust pipe and passing it to said detector; and means for connection between said detector and the suction air intake for passing the first and second part streams after passage through said measuring means to the suction air intake.

16. Apparatus as recited in claims 11 or 15, wherein said means for adding to the first part stream comprises means for adding a liquid combustible material to the first part stream, said liquid combustible material adding means comprising a wick saturator disposed in the first part stream flow and for operative connection to a source of liquid combustible material.

17. Apparatus for analyzing exhaust gas from an exhaust pipe of an internal combustion engine having a suction air intake for combustible or combustion-supporting constituents, comprising:

a detector including means for separating a gas stream into a plurality of part streams, including first and second part streams, means for adding to the first part stream whichever of a combustible or combustion-supporting constituent it is deficient in, means for subjecting the first stream after such addition, and for subjecting the second untreated stream, to conditions effective to cause mutual reaction of combustible and combustion-supporting constituents, means for measuring the temperature difference between the first and second part streams after being acted upon by said subjecting means, and means for heating the exhaust gas, before passage thereof to said subjecting means, to a temperature sufficient to react any residual oxygen and unburnt combustibles in the exhaust gas stream;

means for connection between said detector and the exhaust pipe for withdrawing a sample stream of gas from the exhaust pipe and passing it to said detector; and means for connection between said detector and the suction air intake for passing the first and second part streams after passage through said measuring means to the suction air intake.

18. Apparatus as recited in claim 17 wherein the internal combustion engine is operated at an air to fuel weight ratio in the range 14.8 to 17.0.

19. Apparatus as recited in claim 17 wherein said means for adding to the first part stream comprises a wick saturator disposed in the first part stream flow and operatively connected to a source of liquid combustible material.

20. Apparatus as recited in claim 17 wherein said suction air intake comprises an inlet pipe of a constant pressure drop carburetor.

21. Apparatus as recited in claims 11 or 15, wherein said means for adding to the first part stream comprises means for adding a liquid combustible material, and comprises a wick saturator operatively connected to a source of liquid combustible material.

22. Apparatus as recited in claims 11, 15 or 17 wherein said means for measuring the temperature difference between the first and second part streams comprises: a first electric resistance heating element disposed in the first part stream; a second electric resistance heating element disposed in the second part stream; means for feeding an electric current of predetermined magnitude to said second heating element; means for feeding no or a smaller current to said first heating element, adjusting the current until the temperatures measured in the streams are equal or differ by a specified amount; and means for comparing the magnitudes of the current fed to the first and second heating elements.

23. An apparatus as recited in claim 22 wherein each of said electric resistance heating elements acts as a heater, catalyst, and temperature sensor.

* * * * *